(12) United States Patent
Jonsson

(10) Patent No.: US 11,992,633 B2
(45) Date of Patent: May 28, 2024

(54) INTRAVASCULAR CATHETER DEVICE

(71) Applicant: ANESTEASY AB, Uppsala (SE)

(72) Inventor: Ove Jonsson, Uppsala (SE)

(73) Assignee: ANESTEASY AB, Uppsala (SE)

( * ) Notice: Subject to any disclaimer, the term of this patent is extended or adjusted under 35 U.S.C. 154(b) by 200 days.

(21) Appl. No.: 17/768,443

(22) PCT Filed: Oct. 9, 2020

(86) PCT No.: PCT/EP2020/078365
§ 371 (c)(1),
(2) Date: Apr. 12, 2022

(87) PCT Pub. No.: WO2021/078536
PCT Pub. Date: Apr. 29, 2021

(65) Prior Publication Data
US 2023/0023045 A1 Jan. 26, 2023

(30) Foreign Application Priority Data
Oct. 23, 2019 (SE) .................................... 1951198-9

(51) Int. Cl.
A61M 25/06 (2006.01)
A61M 25/00 (2006.01)

(52) U.S. Cl.
CPC .... A61M 25/0606 (2013.01); A61M 25/0612 (2013.01); A61M 2025/0006 (2013.01); A61M 2025/0008 (2013.01)

(58) Field of Classification Search
CPC .......... A61M 25/0606; A61M 25/0612; A61M 2025/0006; A61M 2025/0008

USPC ......................................................... 604/110
See application file for complete search history.

(56) References Cited

U.S. PATENT DOCUMENTS

2011/0224617 A1* 9/2011 Miner ................ A61M 25/0631
604/164.08
2017/0120011 A1* 5/2017 Burkholz .......... A61M 25/0637

FOREIGN PATENT DOCUMENTS

| KR | 10-2018-010874 A | 10/2018 |
| WO | WO 2015/136423 A1 | 9/2015 |
| WO | WO 2017/074682 A1 | 5/2017 |
| WO | WO 2017/136630 A1 | 8/2017 |
| WO | WO 2017/143176 A1 | 8/2017 |

OTHER PUBLICATIONS

Office Action issued Dec. 22, 2023 for Korean application No. 10-2022-7015726.

* cited by examiner

Primary Examiner — Phillip A Gray
(74) Attorney, Agent, or Firm — Stites & Harbison PLLC; Richard S. Myers, Jr.

(57) ABSTRACT

The disclosure relates to a catheter device (1) comprising a catheter (2) and a hypodermic introducer needle (3), wherein an extended portion (19) of the hypodermic introducer needle (3) is provided with ribs (23, 23a) that circumvent said extended portion, and a proximal end (5) of the catheter (2) is provided with a locking flange (25) adapted to engage with the ribs (23, 23a), such that each rib engaging with the locking flange (25) will provide a tactile indication to the user of the advancement of the catheter (2) in relation to the needle (3).

8 Claims, 6 Drawing Sheets

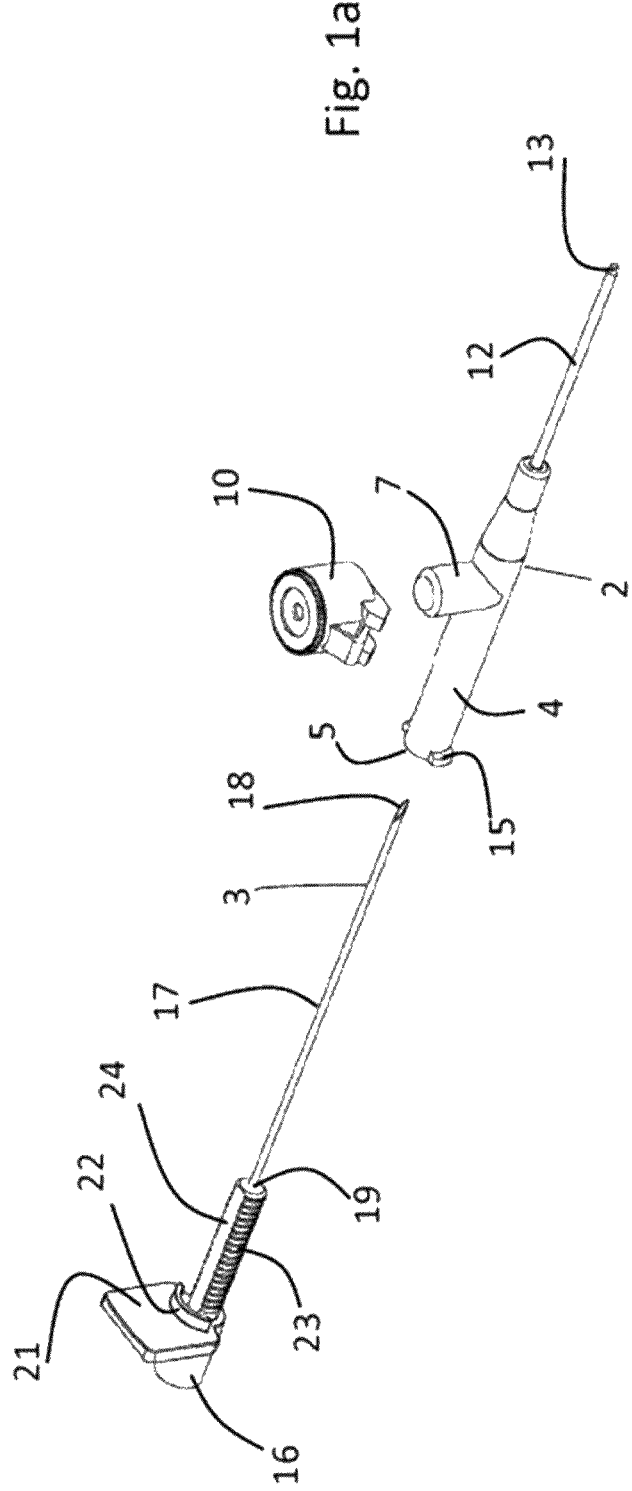

ial Stage Application of
INTRAVASCULAR CATHETER DEVICE

CROSS REFERENCE TO RELATED APPLICATIONS

This application is a § 371 National Stage Application of PCT/EP2020/078365 filed Oct. 9, 2020, which claims priority to SE 1951198-9 filed Oct. 23, 2019.

FIELD OF THE INVENTION

The present invention relates to a catheter device comprising a catheter and a hypodermic introducer needle. More specifically, the disclosure relates to a catheter device comprising a catheter and a hypodermic introducer needle as defined in the introductory parts of claim 1.

BACKGROUND ART

Intravascular catheter devices are known within the art and commonly used to provide access into subcutaneous blood vessels, such as veins, to introduce medication, drugs, chemotherapy, nutrition and/or any other fluids into a subject. SE 355 946 discloses a basic type of infusion cannula assembly that is still widely used. The catheters are normally flexible or semi-flexible in order to be fitted within the blood vessel. As the flexible or semi-flexible catheter is incapable of piercing the skin of a subject, an introducer needle is inserted into the lumen of the catheter such that a bevelled tip of the needle is exposed beyond the distal tip end of the catheter. By inserting the bevelled tip of the needle through the skin and into the targeted blood vessel, the vasculature of a patient is accessed. The insertion into a blood vessel by the needle is indicated by the appearance of blood in a chamber in a needle head. Once the bevelled tip of the needle is inserted into the blood vessel such that blood appears in the chamber, the catheter and the needle are advanced distally into the blood vessel until the desired position of the catheter is achieved. Once the catheter is properly positioned, the needle is removed by pulling the needle proximally from the catheter and the needle is thereafter discarded.

One common problem when inserting catheters is that once blood appears in the chamber, and the needle and catheter are further advanced distally, there is a risk of puncturing the blood vessel further and thereby exiting the blood vessel through an opposite blood vessel wall. This will lead to the catheter not being properly placed. However, this may be difficult to detect, and often leads to discomfort for the patient before being discovered. Once detected, the improperly positioned catheter must be discarded, and the entire procedure has to be repeated with a new catheter device, leading to great discomfort and additional pain for the patient, as well as a negative economic effect due to waste of medical material.

One common practice to avoid the above-mentioned problem is to "hood" the needle once the blood vessel has been accessed. "Hooding" involves maintaining a stationary position of the needle while simultaneously distally motioning the partially inserted catheter, such that the bevelled needle tip is withdrawn into the inner lumen of the catheter. Once the bevelled needle tip is hooded, the catheter device is advanced distally into the vein into a desired position.

One problem with this technique is when the bevelled needle tip has just pierced the blood vessel enough for blood to appear in the needle chamber, but not completely entered the blood vessel. The hooding may then lead to the catheter sliding along the exterior of the blood vessel. Consequently, the catheter is not properly placed in the blood vessel. This will lead to a need to repeat the procedure, having the same consequences as stated above.

Furthermore, hooding is performed blindly as the user cannot see the subcutaneous position of the needle or the catheter in the blood vessel. The bevelled needle tip may therefore be overhooded or underhooded. Underhooding means that a portion of the bevelled needle tip is still exposed beyond the tip of the catheter, risking puncturing a blood vessel further such as mentioned above. Overhooding means that the bevelled needle tip is overdrawn proximally into the lumen of the catheter, leaving the flexible or semi-flexible tip of the catheter unsupported by the needle. The unsupported portion of the catheter may then risk being bent, nicked, or otherwise obstructed while being advanced into the blood vessel. This may lead to insufficient administration of fluids and/or medication through the lumen.

Once the bevelled needle tip is hooded and in a subcutaneous position, the bevelled needle tip may not be pushed back distally into an exposed position where the bevelled needle tip protrudes distally of the catheter tip end, as this may cause the bevelled needle tip to cut off or tear off a part of the catheter tip end. Thus, when discovering that the catheter is not properly positioned after having hooded the bevelled needle tip, the improperly positioned catheter must be discarded, and the entire procedure has to be repeated with a new catheter device, leading to great discomfort and additional pain for the patient, as well as a negative economic effect due to waste of medical material.

SUMMARY

It is an object of the present invention to mitigate, alleviate or eliminate one or more of the above-identified deficiencies and disadvantages in the prior art and solve at least the above-mentioned problem. The inventor has noticed all the problems listed above that may occur when inserting intravenous catheters. In particular, un-experienced users may have a high frequency of improperly positioned catheters. Thus, the inventor has identified an objective of developing an intravenous catheter device that may guide the user and control the insertion process of a catheter such that the problems above are avoided. Another objective of the inventor has been to develop an intravenous catheter device that is easy to use, and does not substantially change the practice compared to today.

According to a first aspect there is provided a catheter device having an axis A-A, a lower side adapted to face a patient, and an upper side opposite the lower side adapted to face away from the patient, the catheter device comprising a catheter and a hypodermic introducer needle;
   the catheter comprising an axially elongated housing having a proximal open end adapted to receive a coupling mechanism or a plug, the housing further comprising an internal passage, a connecting port with an internal orifice arranged on the upper side of the catheter, protrusion members on the outer surface of the proximal open end, and the catheter further comprising a flexible catheter tube connected to the elongated housing, the flexible catheter tube comprising a distal tip end and a lumen, the lumen being in fluid communication with the internal passage of the housing;
   the introducer needle comprising a proximal head, a hollow needle having a distal bevelled tip, an extended portion connecting the needle with the head and adapted to engage with the proximal end of the catheter when the needle is inserted into the catheter, the head comprising an axial channel in fluid communication with the interior of the hollow needle, a grip plate arranged on the head and extending in a direction perpendicular to the axial direction, and an engagement member arranged on the grip plate and protruding distally from the grip plate, the catheter and needle being arranged such that when the needle is inserted into the catheter, the grip plate is directed towards the upper side of the catheter and aligned with the connection port, and wherein the protrusion members on the proximal end of the catheter are adapted to engage with the engagement member on the grip plate to prevent the needle from rotating around the axis A-A in relation to the catheter, wherein the extended portion of the needle is provided with ribs that circumvent the extended portion radially from the axis A-A, and the proximal end of the catheter is provided with a locking flange, adapted to engage with the ribs on the extended portion of the needle when the catheter is motioned distally in relation to the needle.

According to one embodiment, the extended portion of the needle comprises a chamfered surface along one side of the entire extended portion, leading to a cross-sectional U-shape of the extended portion.

According to one embodiment, the ribs are provided with indicators in order to indicate the position of the bevelled tip of the needle in relation to the distal end of the catheter tube.

According to one embodiment, the indicators comprises marking of a rib that will correspond to the catheter being advanced a specified distance, providing a visual indication for the user, in addition to a tactile indication provided by each rib being pulled over and engaging with the locking flange.

According to one embodiment, the ribs comprises indicators to indicate at least the advanced positions of
a) the catheter being advanced a distance d, said distance d corresponding to the length of the bevelled tip of the needle, and
b) the catheter being advanced a distance D, said distance D corresponding to>the length of the bevelled tip of the needle, such as 2× the length of the bevelled tip, or more.

The present invention will become apparent from the detailed description given below. The detailed description and specific examples disclose preferred embodiments of the invention by way of illustration only. Those skilled in the art understand from guidance in the detailed description that changes and modifications may be made within the scope of the invention.

Hence, it is to be understood that the herein disclosed invention is not limited to the particular component parts of the device described or steps of the methods described since such device and method may vary. It is also to be understood that the terminology used herein is for purpose of describing particular embodiments only, and is not intended to be limiting. It should be noted that, as used in the specification and the appended claim, the articles "a", "an", "the", and "said" are intended to mean that there are one or more of the elements unless the context explicitly dictates otherwise. Thus, for example, reference to "a unit" or "the unit" may include several devices, and the like. Furthermore, the words "comprising", "including", "containing" and similar wordings does not exclude other elements or steps.

Definitions

The term "user" is to be interpreted as a caregiver that is to perform placing catheters or other medical treatments, preparations, operations, etc. on a patient.

The term "distal" is to be interpreted as referring to a position or location away from the user. The term "distally" is to be interpreted as referring to a motion leading away from the user.

The term "proximal" is to be interpreted as referring to a position or location close to user. The term "proximally" is to be interpreted as referring to a motion leading towards the user.

The terms "vessel" or "blood vessel" are to be interpreted as any vessel within a patient. It may relate to an artery or a vein.

The term "bevel length" as herein discussed encompasses the entire bevel length, comprising all of any bevelled surfaces of a needle tip.

BRIEF DESCRIPTIONS OF THE DRAWINGS

FIG. 1a shows a perspective view of the parts comprised in the catheter device according to an embodiment of the present disclosure. FIG. 1b shows a cross-sectional view of the catheter device as shown in FIG. 1a upon assembly. FIG. 1c shows a cross-sectional view in close-up of a part of the catheter device encircled in FIG. 1b.

FIG. 2b shows a cross-sectional view in close-up of a part of the catheter device encircled in FIG. 2a.

FIG. 4b shows a cross-sectional view of part of the catheter device encircled in FIG. 4a.

DETAILED DESCRIPTION

Figure 1B:
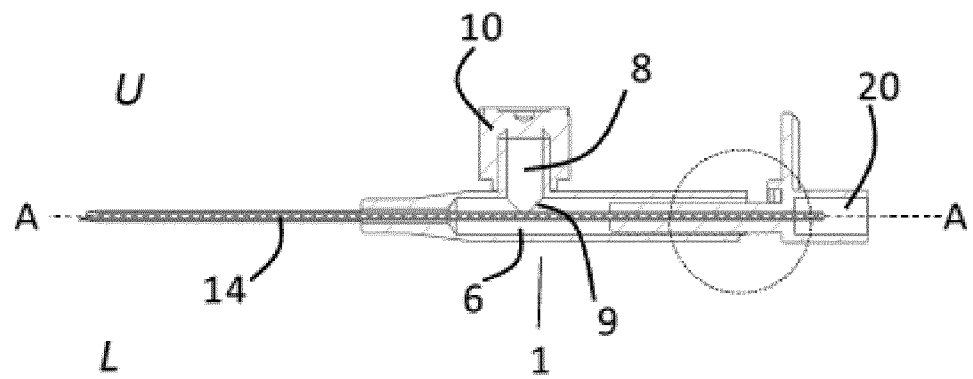

The above objects, as well as additional objects, features and advantages of the present invention will be more fully appreciated by reference to the following illustrative and non-limiting detailed description of example embodiments of the present invention, when taken in conjunction with the accompanying drawings.

The catheter device according to the present disclosure has an axis A-A, a lower side adapted to face a patient, and an upper side opposite the lower side adapted to face away from the patient. The catheter device comprises a catheter and a hypodermic introducer needle.

The catheter comprises an axially elongated housing having a proximal open end adapted to receive a coupling mechanism or a plug. The proximal end may for instance be provided with a female Luer Lock fitting as a coupling mechanism, for easy fitting with syringes etc. Through the coupling mechanism, the catheter may be coupled to an infusion device or any other medical equipment that is common to connect with a catheter. The housing further comprises an internal passage, a connecting port with an internal orifice arranged on the upper side of the catheter. The connecting port may for instance be used for injecting drugs or pharmaceuticals into an infusion liquid being perfused into a patient via the catheter. The housing further comprises protrusion members on the outer surface of the proximal open end in order to engage with and lock the plug or coupling mechanism disclosed above. The catheter further comprises a flexible catheter tube connected to the elongated housing, the flexible catheter tube comprising a distal tip end and a lumen, the lumen being in fluid communication with the internal passage of the housing. The flexible catheter tube is the part of a catheter that is placed in a blood vessel, and must be flexible in order to not injure or puncture the blood vessel into which it is inserted.

The introducer needle comprises a proximal head, a hollow needle having a distal bevelled tip and an extended portion connecting the needle with the head. The extended portion is adapted to engage with the proximal end of the catheter when the needle is inserted into the catheter. The head comprises an axial channel in fluid communication with the interior of the hollow needle, and a grip plate arranged on the head and extending in a direction perpendicular to the axial direction, and an engagement member arranged on the grip plate and protruding distally from the grip plate.

The catheter and the introducer needle, apart from the hypodermic hollow needle, are typically manufactured by a synthetic polymer material that is transparent or semi-transparent. Typically, the material for manufacturing may be a polyurethane, or polytetrafluoroethylene such as FEP. The hypodermic hollow needle is normally manufactured of stainless steel, said steel optionally being plated.

The catheter and needle are arranged such that when the needle is inserted into the catheter, the grip plate is directed towards the upper side of the catheter and aligned with the connection port. Furthermore, the protrusion members on the proximal end of the catheter are adapted to engage with the engagement member on the grip plate to prevent the needle from rotating around the axis A-A in relation to the catheter.

The extended portion of the needle is provided with ribs that circumvent the extended portion radially from the axis A-A. The proximal end of the catheter is provided with a locking flange, adapted to engage with the ribs on the extended portion of the needle when the catheter is motioned distally in relation to the needle. For each rib engaging with the locking flange, a tactile indication is being provided to the user. The first rib to engage with the locking flange is preferably positioned distally of the most distal point of the engagement member on the grip plate, or at the same position along the A-A axis as the most distal point of the engagement member on the grip plate.

The extended portion of the needle provided with ribs may further comprise a chamfered surface along one side of the entire extended portion, leading to a cross-sectional U-shape of the extended portion. Thereby a rotation of the needle will enable re-entry of the needle into the catheter, as the flat chamfered surface of the extended portion will not engage with the locking flange. Thus, the needle may be re-advanced into the catheter. This may be useful if an introducer needle is removed from the catheter by accident. However, more importantly, this is crucial for being able to introduce the introducer needle into the catheter at assembly of the catheter device. However, rotation of the needle to reinsert the needle into the catheter must never be done if the catheter device is already inserted into a patient, for the reasons given above in the present disclosure.

The ribs may be provided with indicators in order to indicate the position of the bevelled tip of the needle in relation to the distal end of the catheter tube. The indicators thus comprises marking of a rib that will correspond to the catheter being advanced a specified distance, providing a visual indication for the user, in addition to a tactile indication provided by each rib being pulled over and engaging with the locking flange. The marking of a rib may comprise a symbol, letter, number or colour, or any other suitable marking.

The indicators may preferably indicate at least the advanced positions of a) the catheter being advanced a distance d, the distance d corresponding to the length of the bevelled tip of the needle, and b) the catheter being advanced a distance D, the distance D corresponding to>the length of the bevelled tip of the needle, such as 2× the length of the bevelled tip, or more. The device may comprise additional indicators correlating to other distances that are advantageous to indicate during the use of the catheter device according to the present disclosure.

The catheter device is used in the same manner as traditional catheter devices. Thus, the catheter device is positioned against the skin of a patient, keeping the axis A-A almost in parallel with the skin surface, slightly tilted so that the distal bevelled tip of the introducer needle is in contact with the skin, while the proximal end of the catheter and the head of the introducer needle is kept at a small height from the skin surface. Thereafter the catheter device is advanced distally so that the distal bevelled tip perforates the skin and eventually also perforates a target blood vessel. The user will know that a blood vessel has been perforated by the distal bevelled tip as blood will then enter the introducer needle and appear in the axial channel of the head of the needle. Thus, the user will visually observe blood appearing in the head of the needle through the transparent or semi-transparent material. Once blood enters the axial channel, the needle is drawn proximally into the lumen of the catheter, or preferably, the catheter is motioned distally while keeping the needle still in relation to the patient, such that the bevelled tip of the needle will become hooded by the catheter tip end. Once the bevelled tip of the needle is hooded by the catheter tip end, the ribs on the extended portion have engaged with the locking flange, thereby preventing any distal motion of the needle in relation to the catheter. It is thus at this stage possible to further advance the entire catheter device by merely pushing the needle distally. Due to the engagement of the ribs with the locking flange, there is no risk of the needle protruding past the catheter tip end by pushing the needle. Thereby there is little or no risk of the bevelled tip cutting or tearing off a part of the catheter tip end.

For a catheter device comprising indicators as disclosed above, the catheter is motioned proximally so that a first indicator is reached, whereby the catheter is motioned from a retracted proximal position to an advanced distal position in relation to the needle. This may mean that the catheter has been advanced a distance d in relation to the needle, where the distanced is equal to the length of the distal bevelled tip of the needle. Hence, the distal bevelled tip of the needle has been hooded by the catheter tip end. At this point of the procedure, the bevelled tip of the needle may not be motioned distally to protrude from the distal tip end of the catheter. The ribs engaging with the locking flange will prevent the needle from being motioned back into the catheter, and prevent any accidental reinsertion of the needle into the catheter, as this may cause the bevelled tip to cut or tear off a small piece of the catheter tube as discussed above. Thus, reaching the first indicator is also a point of no return for the catheter device when introduced into a patient. If anything is discovered to be incorrect in connection with the placement of the catheter, the entire catheter device must be discarded.

Thus, a rib which upon engagement with the locking flange will result in the catheter being motioned distally a distance d, and optionally a rib which upon engagement with the locking flange will result in the catheter being motioned distally a distance D, may be marked. The markings may be the same or different. The first marking being located most proximal on the introducer needle, and closest to the grip plate, will indicate a distance d, and any further markings being located more distally, and farther from the grip plate, will indicate one or more distances D.

The manufacture and packaging of the catheter device according to the present disclosure should be in accordance with regulatory rules and guidelines for use in the healthcare system. Any device that is intended to be used within healthcare and come in contact with a patient and/or bodily fluids must follow such regulatory rules and guidelines.

The present invention will now be described with reference to the accompanying drawings, in which preferred example embodiments of the invention are shown. The invention may, however, be embodied in other forms and should not be construed as limited to the herein disclosed embodiments. The disclosed embodiments are provided to fully convey the scope of the invention to the skilled person.

Figure 1C:
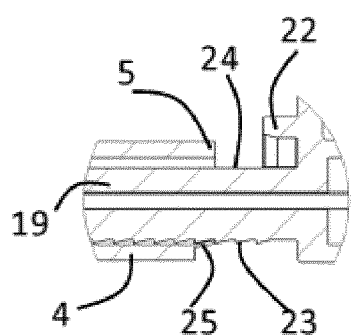

FIGS. 1a-c illustrates a catheter device according to the present disclosure. having a central axis A-A, a lower side (L) adapted to face a patient, and an upper side (U) opposite the lower side (L) adapted to face away from the patient, the catheter device 1 comprising a catheter 2 and a hypodermic introducer needle 3. The catheter 2 comprises an axially elongated housing 4 having a proximal open end 5 adapted to receive a coupling mechanism or a plug. The housing 4 further comprises an internal passage 6, a connecting port 7 with an internal orifice 8 arranged on the upper side of the catheter, said orifice 8 being in connection with the internal passage 6 by a non-return valve 9. A plug 10 may be fitted over the connecting port 7. Protrusion members 15 are arranged on the outer surface of the proximal open end 5. The catheter 2 further comprises a flexible catheter tube 12 connected to the elongated housing 4, the flexible catheter tube 12 comprising a distal tip end 13 and a lumen 14, wherein the lumen 14 is in fluid communication with the internal passage 6 of the housing 4. The introducer needle 3 comprises a proximal head 16, a hollow needle 17 having a distal bevelled tip 18, an extended portion 19 connecting the needle 17 with the head 16 and adapted to engage with the proximal end 5 and the elongated housing 4 of the catheter 2 when the needle 3 is inserted into the catheter 2. The head 16 comprises an axial channel 20 in fluid communication with the interior of the hollow needle 17, a grip plate 21 arranged on the head 16 extending in a direction perpendicular to the axial direction of the catheter device 1, and an engagement member 22 arranged on the grip plate 21 and protruding distally from the grip plate 21. The catheter 2 and needle 3 are arranged in the catheter device 1 such that when the needle 3 is inserted into the catheter 2, the grip plate 21 is directed towards the upper side of the catheter 2 and aligned with the connection port 7. The protrusion members 15 on the proximal end 5 of the catheter 2 are typically adapted to engage with the engagement member 22 on the grip plate 21 to prevent the needle 3 from rotating around the axis A-A in relation to the catheter 2.

The extended portion 19 of the needle 3 is provided with ribs 23 that circumvent the extended portion 19 radially from the axis A-A, and the proximal end 5 of the catheter 2 is provided with a locking flange 25, adapted to engage with the ribs 23 on the extended portion 19 of the needle 3 when the catheter 2 is motioned distally in relation to the needle 3.

In the embodiment shown in the all figures, the extended portion 19 of the needle 3 comprises a chamfered surface 24 along one side of the entire extended portion 19, leading to a cross-sectional U-shape (not shown) of the extended portion 19.

Figure 2A:
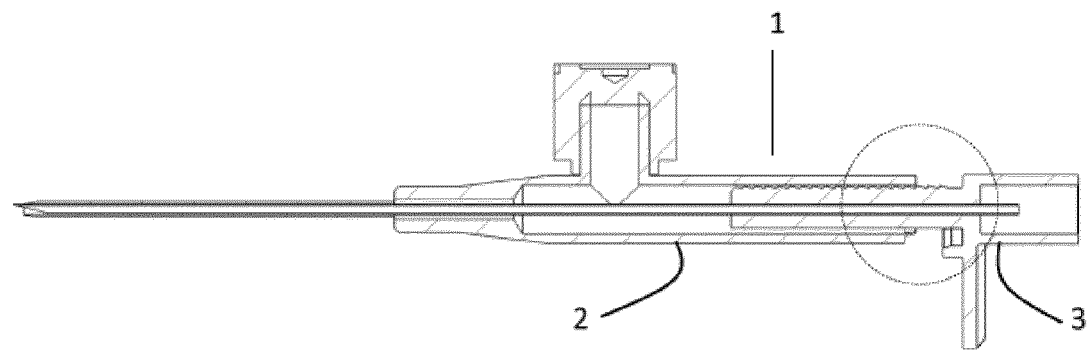
FIG. 2a shows cross-sectional views of the catheter device, illustrating the function of the chamfered surface.
Figure 2B:
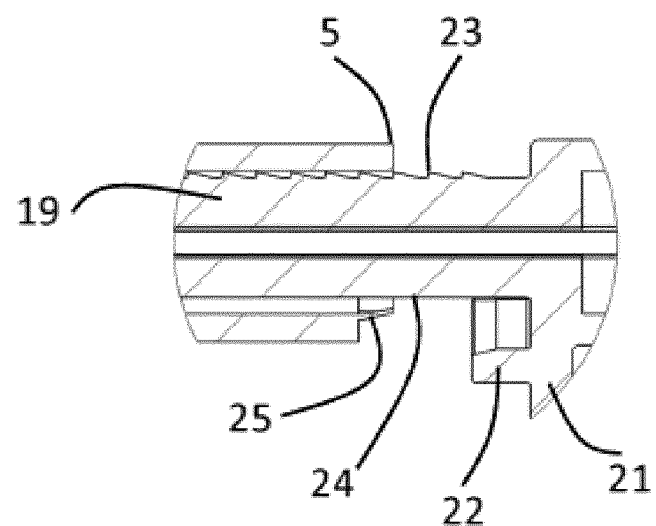

FIGS. 2a and 2b illustrates the function of the chamfered surface 24. By rotating the needle 3 so that the chamfered surface 24 is aligned with the locking flange 25, it is possible to reinsert the needle 3 into the catheter 2, or to reposition the catheter 2 by pulling it proximally in relation to the needle 3. The exact positioning of the locking flange 25 and the chamfered surface 24 is not of importance, as long as they are not aligned with each other when the grip plate is facing the upper side and aligned with the connecting port on said upper side, i.e. the arrangement of the catheter device for insertion of the catheter into a patient. The locking flange 25 must not be positioned such that it prevents a user from connecting a plug, connector or infusion device to the catheter 2.

Figure 3A:
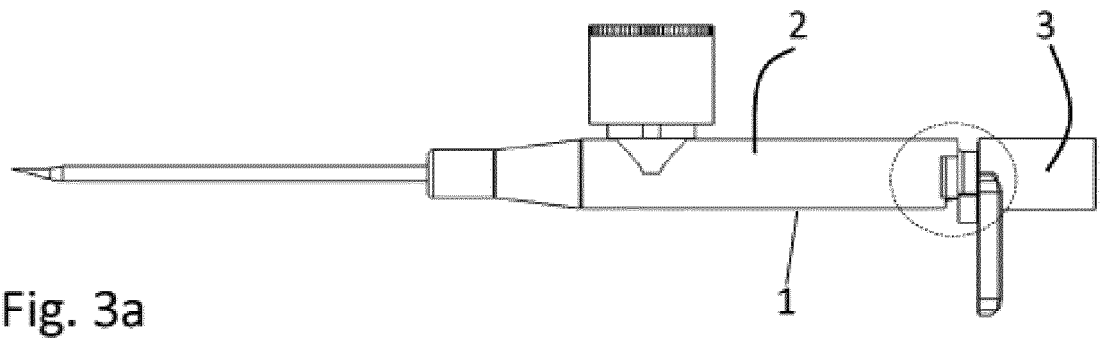
FIG. 3a shows a side view of the catheter device, further illustrating the function of the chamfered surface.
Figure 3B:
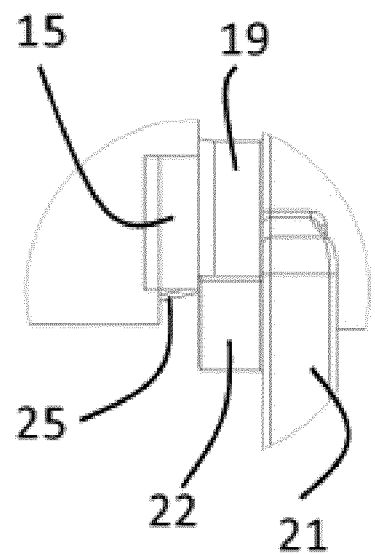
FIG. 3b shows a view in close-up of part of the catheter device encircled in FIG. 3a, and FIG. 3c a cross-sectional view in close-up of the same part of the catheter device as FIG. 3b.
Figure 3C:
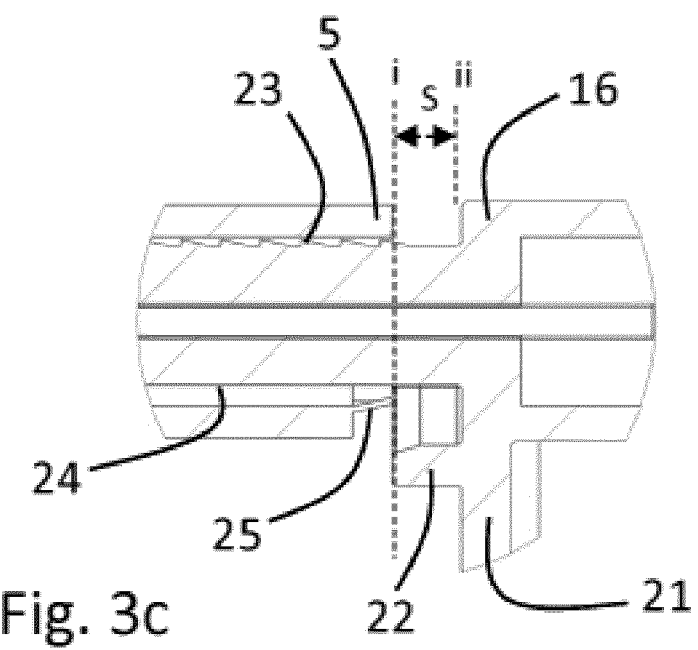

FIG. 3a-c illustrates that when the needle 3 is reinserted into the catheter 2, by rotating the needle 3 as disclosed above in relation to FIG. 2a-b, the insertion of the needle 3 will stop when the engagement member 22 reaches the locking flange 25, and optionally also the protrusion members 15. The locking flange 25 and optionally the protrusion members 15 will thus block further advancement of the engagement member 22, and hence of the needle 3. As is clear from in particular 3a and 3c, the needle 3 is at this point not completely inserted into the catheter 2. There is still a space S between the edge of the proximal end 5 of the catheter 2, indicated by the line i, and the edge of the head 16 of needle 3, indicated by the line ii.

However, the locking flange 25 will at this point have passed proximal of the first rib 23 which is positioned axially either at the same position as the engagement member 22, or more distally than the engagement member 22. As seen in FIG. 3c, the edge of the first rib is somewhat distal in relation to the engagement member 22, the position of which is indicated by the line i. As disclosed above, the first rib to engage with the locking flange is preferably positioned distally of the most distal point of the engagement member on the grip plate, or at the same position axially as the most distal point of the engagement member on the grip plate.

Figure 4A:
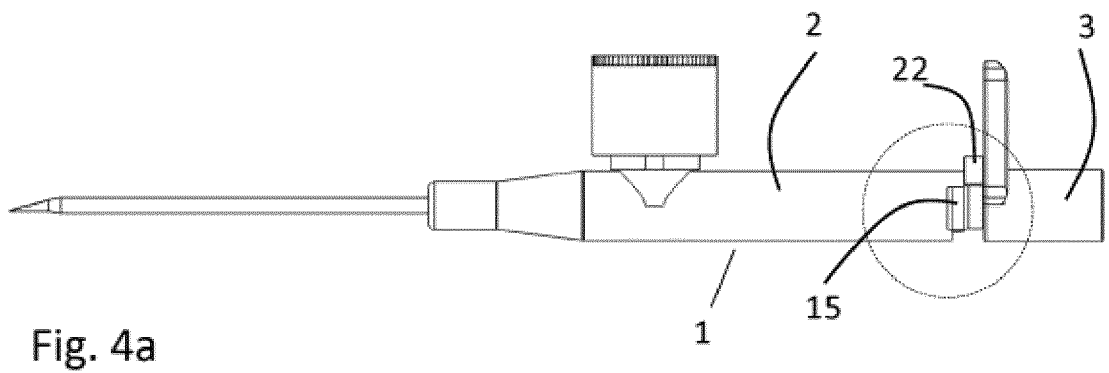
FIG. 4a shows a side view of the catheter device illustrating further the function of the chamfered surface and the ridges.
Figure 4B:
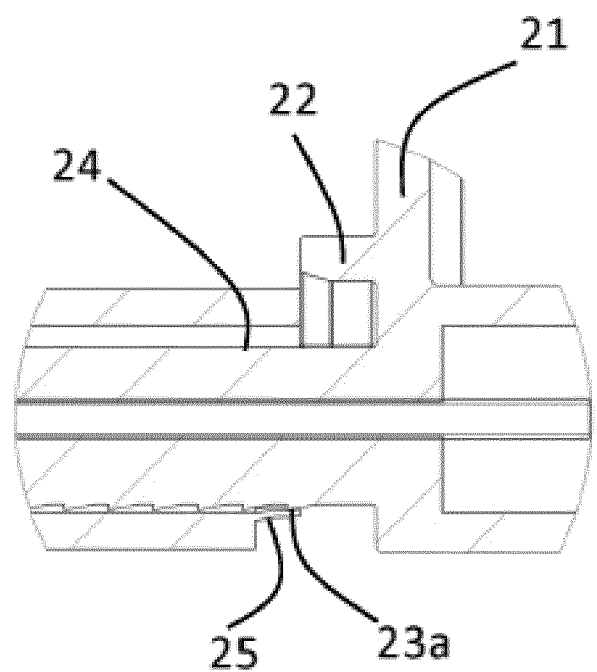

FIGS. 4a and 4b illustrates that in the position where the engagement member 22 touches the locking flange 25 as illustrated in FIGS. 3a-c, it is possible to rotate the needle 3 back into the position for use of the catheter device 1, without any rib 23 engaging with the locking flange 25. The most proximal rib 23a does not at this stage interact with the locking flange 25, and thereby does not interfere with a complete insertion of the needle into the catheter. The positioning of the protrusion members 15 needs to be such that they will not interfere with the rotation of the needle 3 at this stage. Rather, they may preferably be positioned to aid the rotation of the needle 3, such that the engagement member 22 will be positioned immediately adjacent to the protrusion member 15, as indicated in FIG. 3b, so that a distal surface of the engagement member 22 will slide against a proximal surface of the protrusion member 15.

Figure 5A:
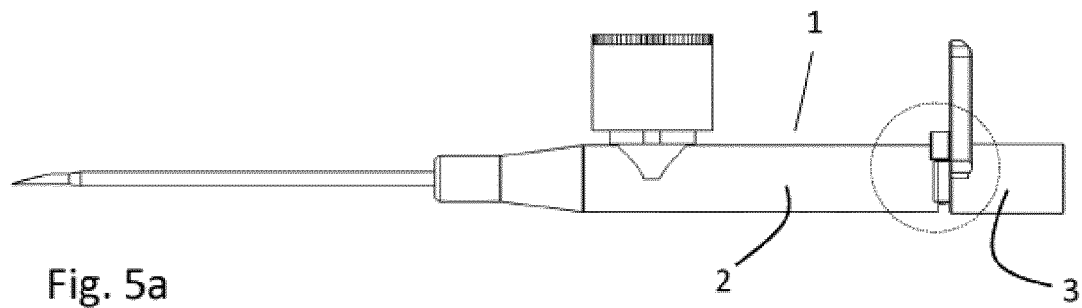
FIG. 5a shows a side view of the catheter device ready for use.
Figure 5B:
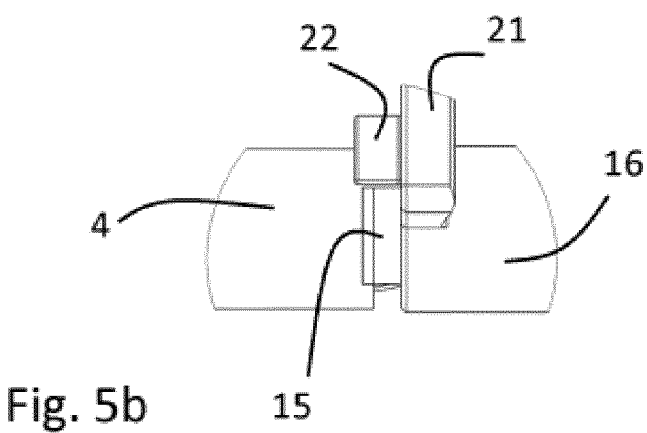
FIG. 5b shows a view in close-up of part of the catheter device encircled in FIG. 5a, and FIG. 5c a cross-sectional view in close-up of the same part of the catheter device as FIG. 5b.
Figure 5C:
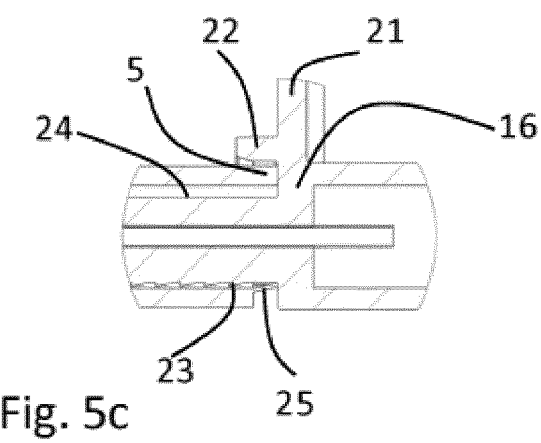

FIG. 5*a-c* illustrates the catheter device 1 when the needle 3 has been fully inserted into the catheter 2. When the needle 3 has been rotated from the position illustrated in FIGS. 3*a-c*, to a position illustrated in FIGS. 4*a* and *b*, the needle 3 may be further motioned distally to that the needle 3 is fully inserted into the catheter. The head 16 of the needle 3 then engages with the proximal edge of the proximal open end 4 of the catheter 2. Thus, at this point the engagement member 22 is protruding past the edge of the proximal open end 4 of the catheter 2 as seen in FIG. 5*c*. The engagement member 22 is furthermore blocked from rotation around the A-A axis by the protrusion members 15. This is typically the arrangement of the catheter device 1 in which it is delivered to the user.

The exact positioning of the locking flange 25 and the chamfered surface 24 is not of importance, as long as they are not aligned when the grip plate 21 is facing the upper side and aligned with the connecting port 7 on said upper side, i.e. the arrangement of the catheter device needle 3 for insertion of the catheter 2 into a patient.

The person skilled in the art realizes that the present invention is not limited to the preferred embodiments described above. The person skilled in the art further realizes that modifications and variations are possible within the scope of the appended claims. For example, the exact shape of the ribs and the locking flange are possible to vary without departing from scope of the appended claims. Additionally, variations to the disclosed embodiments can be understood and effected by the skilled person in practicing the claimed invention, from a study of the drawings, the disclosure, and the appended claims.

The invention claimed is:

1. A catheter device (1) having an axis A-A, a lower (L) side adapted to face a patient, and an upper side (U) opposite the lower side adapted to face away from the patient, said catheter device (1) comprising a catheter (2) and a hypodermic introducer needle (3),
    the catheter (2) comprising an axially elongated housing (4) having a proximal open end (5) adapted to receive a coupling mechanism or a plug, said housing (4) further comprising an internal passage (6), a connecting port (7) with an internal orifice (8) arranged on the upper side of the catheter (2), protrusion members (15) on an outer surface of the proximal open end (5), and said catheter (2) further comprising a flexible catheter tube (12) connected to the axially elongated housing (4), said flexible catheter tube (12) comprising a distal tip end (13) and a lumen (14), said lumen (14) being in fluid communication with the internal passage (6) of the housing (4);
    the hypodermic introducer needle (3) comprising a proximal head (16), a hollow needle (17) having a distal beveled tip (18), an extended portion (19) connecting the hollow needle (17) with the proximal head (16) and adapted to engage with the proximal open end (5) of the catheter (2) when the hypodermic introducer needle (3) is inserted into the catheter (2), said head (16) comprising an axial channel (20) in fluid communication with an interior of the hollow needle (17), a grip plate (21) arranged on the proximal head (16) and extending in a direction perpendicular to an axial direction, and an engagement member (22) arranged on the grip plate (21) and protruding distally from said grip plate (21),
    said catheter (2) and hypodermic introducer needle (3) being arranged such that when the needle (3) is inserted into the catheter (2), the grip plate (21) is directed towards the upper side (U) of the catheter (2) and aligned with the connection port (7), and wherein the protrusion members (15) on the proximal open end (5) of the catheter (2) are adapted to engage with the engagement member (22) on the grip plate (21) to prevent the hypodermic introducer needle (3) from rotating around the axis A-A in relation to the catheter (2),
    wherein the extended portion (19) of the needle (3) is provided with ribs (23, 23*a*) that circumvent the extended portion (19) radially from the axis A-A, and wherein the proximal open end (5) of the catheter (2) is provided with a locking flange (25), adapted to engage with the ribs (23, 23*a*) on the extended portion (19) of the hypodermic introducer needle (3) upon distal motion of the catheter (2) in relation to said needle (3).

2. The catheter device (1) according to claim 1, wherein the extended portion (19) of the hypodermic introducer needle (3) comprises a chamfered surface (24) along one side of an entire extended portion (19), leading to a cross-sectional U-shape of the extended portion (19).

3. The catheter device (1) according to claim 1, wherein the ribs (23, 23*a*) are provided with indicators in order to indicate the position of the distal beveled tip (18) of the needle (3) in relation to the distal end (13) of the catheter tube (12).

4. The catheter device (1) according to claim 1, wherein the indicators comprise marking of a rib (23, 23*a*) that will correspond to the catheter (2) being advanced a specified distance, providing a visual indication for an user, in addition to a tactile indication provided by each rib (23, 23*a*) being pulled over and engaging with the locking flange (25).

5. The catheter device (1) according to claim 1, wherein the ribs (23, 23*a*) comprises indicators to indicate at least the advanced positions of a) the catheter (2) being advanced a distanced, said distance d corresponding to a length of the beveled tip (18) of the hypodermic introducer needle (3), and b) the catheter (2) being advanced a distance D, said distance D corresponding to) the length of the beveled tip (18) of the hypodermic introducer needle (3).

6. The catheter device (1) according to claim 5, wherein said distance D corresponds to at least two times the length of the beveled tip (18).

7. The catheter device (1) according to claim 2, wherein the ribs (23, 23*a*) are provided with indicators in order to indicate the position of the distal beveled tip (18) of the needle (3) in relation to the distal end (13) of the catheter tube (12).

8. The catheter device (1) according claim 7, wherein the indicators comprise marking of a rib (23, 23*a*) that will correspond to the catheter (2) being advanced a specified distance, providing a visual indication for a user, in addition to a tactile indication provided by each rib (23, 23*a*) being pulled over and engaging with the locking flange (25).

* * * * *